United States Patent
Lambino et al.

(10) Patent No.: US 7,452,547 B2
(45) Date of Patent: Nov. 18, 2008

(54) PRODUCT FOR TREATING THE SKIN COMPRISING A POLYAMINE MICROCAPSULE WALL AND A SKIN LIGHTENING AGENT

(75) Inventors: Danilo Lambino, Kogarah (AU); Christine Loh, North Ryde (AU); Roderico Estanislao, San Pedro (PH); Alain Khaiat, Mulan Court (SG)

(73) Assignee: Johnson&Johnson Consumer Co., Inc., Skillman, NJ (US)

( * ) Notice: Subject to any disclaimer, the term of this patent is extended or adjusted under 35 U.S.C. 154(b) by 0 days.

(21) Appl. No.: 10/814,993

(22) Filed: Mar. 31, 2004

(65) Prior Publication Data
US 2005/0226834 A1    Oct. 13, 2005

(51) Int. Cl.
*C11D 3/30* (2006.01)

(52) U.S. Cl. ............... 424/414; 510/130; 510/295; 510/499; 401/132; 401/137; 401/148; 401/196; 514/828; 424/401; 424/489; 424/490

(58) Field of Classification Search ............... 510/130, 510/499, 295; 424/401, 414, 489, 490; 401/132, 401/137, 148, 196; 514/828
See application file for complete search history.

(56) References Cited

U.S. PATENT DOCUMENTS

| | | | |
|---|---|---|---|
| 3,686,701 A * | 8/1972 | Charle et al. .............. 15/104.93 |
| 3,691,270 A | 9/1972 | Charle et al. |
| 3,896,807 A | 7/1975 | Buchalter |
| 4,100,103 A | 7/1978 | Foris |
| 4,251,386 A | 2/1981 | Saeki |
| 4,362,747 A | 12/1982 | Coursen |
| 4,448,704 A * | 5/1984 | Barby et al. .............. 15/104.93 |
| 4,497,843 A | 2/1985 | Errass |
| 4,591,501 A | 5/1986 | Cioca |
| 4,752,496 A * | 6/1988 | Fellows et al. .............. 427/485 |
| 4,878,775 A * | 11/1989 | Norbury et al. .............. 401/132 |
| 5,026,552 A | 6/1991 | Gueret et al. |
| 5,071,706 A | 12/1991 | Soper |
| 5,227,242 A | 7/1993 | Walter et al. |
| 5,466,465 A | 11/1995 | Royds et al. |
| 5,716,599 A | 2/1998 | Golz et al. |
| 5,957,605 A * | 9/1999 | Cohen et al. .............. 401/132 |
| 5,993,857 A * | 11/1999 | Menzel et al. .............. 424/489 |
| 6,120,784 A | 9/2000 | Snyder, Jr. |
| 6,159,493 A | 12/2000 | Chen et al. |
| 6,270,783 B1 * | 8/2001 | Slavtcheff et al. .............. 424/402 |
| 6,303,149 B1 | 10/2001 | Magdassi |
| 6,306,408 B1 * | 10/2001 | Eichhorn et al. .............. 424/401 |
| 6,316,021 B1 | 11/2001 | Gueret |
| 6,337,066 B1 | 1/2002 | Jacquier |
| 6,365,135 B1 | 4/2002 | Philippe et al. |
| 6,410,017 B1 | 6/2002 | Weisgerber et al. |
| 6,429,261 B1 * | 8/2002 | Lang et al. .............. 525/191 |
| 6,503,232 B1 | 1/2003 | Kawai et al. |
| 6,508,604 B1 * | 1/2003 | Bechmann et al. .............. 401/132 |
| 6,521,241 B1 | 2/2003 | Minerath, III et al. |
| 6,550,474 B1 * | 4/2003 | Anderson et al. .............. 128/200.24 |
| 6,551,607 B1 | 4/2003 | Minerath, III et al. |
| 6,641,822 B2 * | 11/2003 | Eichhorn et al. .............. 424/401 |
| 2002/0035046 A1 | 3/2002 | Lukenbach et al. |
| 2002/0197289 A1 | 12/2002 | Chevalier et al. |
| 2003/0027738 A1 | 2/2003 | Delambre et al. |
| 2003/0044366 A1 | 3/2003 | Dole et al. |
| 2003/0082217 A1 | 5/2003 | Afriat et al. |
| 2003/0125222 A1 | 7/2003 | Jahns |
| 2005/0066526 A1 * | 3/2005 | Guimont .............. 30/41 |

FOREIGN PATENT DOCUMENTS

| | | |
|---|---|---|
| EP | 0063875 A2 | 4/1982 |
| EP | 0381057 A2 | 1/1990 |
| EP | 0 365 160 A2 | 4/1990 |
| EP | 0364922 B1 | 9/1992 |
| EP | 1 410 753 A1 | 7/2001 |
| GB | 1304375 * | 1/1973 |
| GB | 2073132 A | 10/1981 |
| JP | 07335151 | 6/1997 |
| JP | 1081612 | 3/1998 |
| JP | 1149635 | 2/1999 |
| JP | 11130624 | 5/1999 |
| JP | 11228340 | 8/1999 |
| JP | 10082967 | 9/1999 |
| JP | 11322538 | 11/1999 |
| JP | 2000-093994 | 3/2000 |
| JP | 2000-128732 A | 5/2000 |
| JP | 2000136112 A | 5/2000 |
| JP | 2000 256162 | 9/2000 |
| JP | 11131791 | 10/2000 |
| WO | WO 97/32567 A1 | 9/1997 |
| WO | WO 00/28961 A1 | 5/2000 |
| WO | WO 00/62763 A2 | 10/2000 |

(Continued)

OTHER PUBLICATIONS

EPO Search Report dated Jul. 18, 2005, for corresponding EP application 05251979.0.

(Continued)

*Primary Examiner*—Charles I Boyer

(57) ABSTRACT

The present invention features a product including a water-insoluble substrate and a plurality of microcapsules comprising a microcapsule wall surrounding a liquid core, and the use thereof.

16 Claims, No Drawings

FOREIGN PATENT DOCUMENTS

| | | |
|---|---|---|
| WO | WO 01/01933 A2 | 1/2001 |
| WO | WO 01/01951 A1 | 1/2001 |
| WO | WO 01/02028 A2 | 1/2001 |
| WO | WO 01/02478 A1 | 1/2001 |
| WO | WO 01/02479 A1 | 1/2001 |
| WO | WO 02/062132 A2 | 8/2002 |
| WO | WO 02/074430 A1 | 9/2002 |
| WO | WO 03/005876 A | 1/2003 |

OTHER PUBLICATIONS

3M—PMU Microcapsules 32 Micron Encapsulated Oils, 2003, St. Paul, MN USA.
The world's tiniest perfume bottles, pp. 30-33.
Product box for Innisfree.
Product box for Lifecella.
Product box for Naturals T zone leaf.
Product box for Naturals U zone leaf.
Product Pouch for Face Mask.
TSC TU-Zone Mask Nourishing Type packaging, publicly available prior to Oct. 7, 2003.
TSC TU-Zone Mask Fresh Type packaging, publicly available prior to Oct. 7, 2003.
Neutrogena® Fine Fairness Mask Hydrating Vitamin C Formula, packaging, publicly available prior to Oct. 7, 2003.
Neutrogena® Hydrating Facial™ Cloth Mask, Relaxing at-Home Facial packaging, publicly available prior to Oct. 7, 2003.

* cited by examiner

PRODUCT FOR TREATING THE SKIN COMPRISING A POLYAMINE MICROCAPSULE WALL AND A SKIN LIGHTENING AGENT

FIELD OF THE INVENTION

The present invention relates to a product and the uses thereof to treat skin.

BACKGROUND OF THE INVENTION

Products such as cleansers and moisturizers formulated with vitamins and other skin benefit agents have been used for many years to treat the skin. Employing a water-insoluble substrate such as wipe or mask to assist in the process of cleansing, moisturizing and delivery of certain benefit agents to the skin is also known. For example, consumers typically use hydrating facial mask products for treatment of various skin conditions as well as to improve the physical appearance and texture of the facial skin. This can be accomplished while the user relaxes, such as in a prone position, while the mask contacts the skin of the face, and provides benefits thereto.

Unfortunately, such products can be limited in their ability to provide multiple benefits to the subject as benefit agents can be incompatible with one another, resulting in premature degradation or poor shelf stability. Furthermore, the multiple benefit agents can be difficult or impossible to incorporate into the mask in a form that is aesthetically pleasing to the user.

It is also particularly challenging to provide a facial mask product that is able to impart an appealing change in color/tone to the skin or impart improved color/tone uniformity that manifests in a particularly short period of time. Thus, it is especially difficult to design product, such as a facial mask, that provides fast-onset benefits related to color/tone in addition to other skin benefits such as those relating to anti-acne, shine control, microbial control, anti-inflammation, anti-oxidation, skin-firming, anti-wrinkle, among other skin benefits.

Therefore, there is a need for a product that is capable of overcoming one or more of the above-mentioned drawbacks.

SUMMARY OF THE INVENTION

The present invention features a product including a water-insoluble substrate and a plurality of microcapsules comprising a microcapsule wall surrounding a liquid core, and the use thereof.

DETAILED DESCRIPTION OF THE INVENTION

It is believed that one of ordinary skill in the art can, based upon the description herein, utilize the present invention to its fullest extent. The following specific embodiments of the invention are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Whenever used, any percentage is weight by weight (% w/w) unless otherwise indicated.

Product

The product of the present invention includes at least one water-insoluble substrate. The product may also include a liquid impregnate. The liquid impregnate may be present in a weight ratio to the water-insoluble substrate that is greater than about 5%, such as greater than about 50%, such as greater than about 65%, such between about 65% and about 95%. Furthermore, the product includes a plurality of microcapsules including a microcapsule wall surrounding a liquid core.

Water-Insoluble Substrate

The product of the present invention includes a water-insoluble substrate. By "water-insoluble" is meant that the substrate, upon immersion in distilled water at 25° C., does not readily dissolve in or readily break apart. Under such immersion, while portions of the water-insoluble substrate may be leachable or readily soluble in the distilled water, at least an other portion of the water-insoluble substrate remains intact. For example, the other portion may be readily manipulated, such as picked up and transported as an interconnected cohesive unit, by a user's hands. In an alternative embodiment of the invention, the water-insoluble substrate may, however, be disintegrated and/or dissolved slowly in the distilled water, i.e., over a period of several hours up to several days.

A wide variety of materials can be used as the water-insoluble substrate. Examples of suitable substrates include, but are not limited to, fibrous substrates such as substrates including or formed from non-woven fibers, woven fibers, hydro-entangled fibers, or air-entangled fibers. The water-insoluble substrate may include natural sponges, synthetic sponges, and polymeric netted meshes.

The water-insoluble substrate may be formed to retain a liquid impregnate (such as by absorbing the liquid impregnate among, along, and/or between fibers comprising the water-insoluble substrate) for a period of time at least as long as from when the product is manufactured to a time when the product is used by a consumer (i.e., a shelf storage period). In this embodiment of the invention, during this shelf storage period the water-insoluble substrate should generally maintain its mechanical integrity such that a user can apply the water-insoluble substrate to the skin and transferring liquid impregnate thereto.

The water-insoluble substrate may be flushable. As used herein, by "flushable" is meant that the substrate will pass through at least 10 feet of waste pipe in two toilet flushes. The material may also be biodegradable.

In one embodiment of the invention, the substrate includes a non-woven material. By "non-woven" is meant that the substrate, or a layer of the substrate, is comprised of fibers that are not woven into a fabric but rather are formed into a sheet, mat, or pad layer. The fibers can either be random (i.e., randomly aligned) or they can be carded (i.e., combed to be oriented in primarily one direction. Furthermore, the non-woven substrate can be composed of a combination of layers of random and carded fibers).

Non-woven substrates may be comprised of a variety of natural and/or synthetic materials. By "natural" it is meant that the materials are derived from plants, animals, insects, or byproducts of plants, animals, and insects. By "synthetic" it is meant that the materials are obtained primarily from various man-made materials or from natural materials, which have been further altered. Non-limiting examples of natural materials useful in the present invention are silk fibers, keratin fibers (such as wool fibers, camel hair fibers) and cellulosic fibers (such as wood pulp fibers, cotton fibers, hemp fibers, jute fibers, and flax fibers).

Examples of synthetic materials include, but are not limited to, those selected from the group containing acetate fibers, acrylic fibers, cellulose ester fibers, cotton fibers, modacrylic fibers, polyamide fibers, polyester fibers, polyolefin fibers, polyvinyl alcohol fibers, rayon fibers, polyurethane foam, and mixtures thereof.

Substrates made from one ore more of the natural and synthetic materials useful in the present invention can be obtained from a wide variety of commercial sources such as Freudenberg & Co. (Durham, N.C. USA), BBA Nonwovens (Nashville, Tenn. USA), PGI Nonwovens (North Charleston, S.C. USA), Buckeye Technologies/Walkisoft (Memphis, Tenn. USA), Sansho Shigyo K.K. (Tosa City, Kouchi, Japan), and Fort James Corporation (Deerfield, Ill. USA).

Methods of making non-woven substrates are also well known in the art. Such methods include, but are not limited to, air-laying, water-laying, melt-blowing, spin-bonding, or carding processes. The resulting substrate, regardless of its method of production or composition, is then generally subjected to at least one of several types of bonding operations to anchor the individual fibers together to form a self-sustaining web. The non-woven substrate can be prepared by a variety of processes including hydro-entanglement, thermally bonding, chemical bonding and combinations of these processes. Moreover, the substrates can have a single layer or multiple layers. In addition, a multi-layered substrate can include film layer(s) (e.g., aperture or non-aperture film layers) and other non-fibrous materials.

Strength or firmness of the non-woven material may be a desirable attribute. This can be achieved, for example, by the addition of binding materials, such as wet strength resins, or the material may be made of polymer binder coatings, stable fibres, e.g. based on cotton, wool, linen and the like. Examples of wet strength resins include, but are not limited to, vinyl acetate-ethylene (VAE) and ethylene-vinyl chloride (EVCL) Airflex emulsions (Air Products, Lehigh, Pa.), Flexbond acrylic polymers (Air Products, Lehigh, Pa.), Rhoplex ST-954 acrylic binder (Rohm and Haas, Philadelphia, Pa.), and Ethylene-vinyl acetate (EVA) emulsion (DUR-O-SET® by National Starch Chemicals, Bridgewater, N.J.). The amount of binding material in the substrate may range from about 5% to about 20%, by weight, of the substrate.

Non-woven materials of increased strength can also be obtained by using the so-called spunlace or hydro-entanglement technique. In this technique, the individual fibers are twisted together so that an acceptable strength or firmness is obtained without the need to use binding materials. The advantage of the latter technique is the excellent softness of the non-woven material.

The basis weight of the water-insoluble substrate may range from about 10 grams per square meter (gsm) to about 100 gsm, such as between about 30 gsm and about 70 gsm. The water-insoluble substrate may have an average thickness that is less than about 5 mm, such as between about 0.1 mm and about 1 mm.

In one embodiment of the invention, the non-woven material includes or is made from a superabsorbent polymer. For the purposes of the present invention, the term "superabsorbent polymer" refers to materials which are capable of absorbing and retaining at least about 10 times their weight in water under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and other material known to the art of absorbent article manufacture.

Additives may also be added in order to increase the softness of the substrates. Examples of such additives include, but are not limited to, polyols such as glycerol, propylene glycol and polyethylene glycol, phthalate derivatives, citric esters, surfactants such as polyoxyethylene (20) sorbitan esters, and acetylated monoglycerides.

Sensory attributes may also be incorporated to the insoluble non-woven substrates. Examples of such sensory attributes include, but are not limited to color, texture, pattern, and embossing of the substrate.

The water-insoluble substrate when laid flat, may cover an area that is from about 100 $cm^2$ to about 1000 $cm^2$, such as from about 200 $cm^2$ to about 500 $cm^2$, such as between about 200 $cm^2$ to about 360 $cm^2$.

The water-insoluble substrate may have a size and shape such that it covers the face of a human user to facilitate placing the water-insoluble substrate about the face of the user. For example, the water-insoluble substrate may have openings for a mouth, nose, and/or eyes of the user. Alternatively, the water-insoluble substrate may have no such openings. Such a configuration without openings may be useful for embodiments of the invention in which the water-insoluble substrate is intended to be draped over a non-facial expanse of skin or if the water-insoluble substrate is intended to be used as wipe. The water-insoluble substrate may have various shapes, such as an angular shape (e.g., rectangular) or an arcuate shape such as circular or oval.

In one embodiment of the invention, the product includes a plurality of water-insoluble substrates of different shapes. In one embodiment of the invention, the product includes a first water-insoluble substrate and a second water-insoluble substrate. The first water-insoluble substrate is shaped for application onto the forehead and the second water-insoluble substrate is shaped for application proximate to the mouth, such as areas above and/or below the lips, the chin, and/or the cheeks. In one embodiment of the invention, the first water-insoluble substrate is also applied to the nose region of the face. The first water-insoluble substrate may have a surface area of from about 100 $cm^2$ to about 200 $cm^2$, such as from about 120 $cm^2$ to about 160 $cm^2$ and the second water-insoluble substrate has a surface area of from about 100 $cm^2$ to about 300 $cm^2$, such as from about 150 $cm^2$ to about 250 $cm^2$. In one embodiment of the invention, the water-insoluble substrate has a low stiffness such that it may, for example, readily drape over or conform to the face or other body parts of the user.

Liquid Impregnate

The product may include a liquid impregnate, such as may be used to moisten the water-insoluble substrate. In one embodiment of the invention, the liquid impregnate is present in an amount of at least about 5% by weight of the weight of the water-insoluble substrate. In other words, if one were to separate the impregnate from the water-insoluble substrate, the ratio of the weight of liquid impregnate removed to the weight of the water-insoluble substrate is greater than about 5%. By having the liquid impregnate present in at least about this ratio, the liquid impregnate may be readily transferred to skin placed in contact with the water-insoluble substrate. To further enhance the transfer of the liquid impregnate to the skin of the user, such as for a hydrating facial mask, the liquid impregnate may be present in a weight ratio to the water-insoluble substrate that greater than about 50%, such as greater than about 65%, such as between about 65% to about 95%.

In another embodiment of the invention, the liquid impregnate is present in a ratio that is less than about 5% by weight of the weight of the water-insoluble substrate or containing no liquid impregnate. Such products may be used for applications where a liquid is applied to them (e.g., water or a liquid skin care product such as a toner or cleanser) prior to application to the skin, such as a cleansing wipe.

The liquid impregnate may include an aqueous phase, an oily/hydrophobic phase, a gel phase, or a mixture of these phases. Microcapusles (described below) may be dispersed within one or more of these phases. In one embodiment, the microcapsules are dispersed in an aqueous phase.

In one embodiment, the liquid impregnate has a viscosity that is less than about 10,000 centipoise (cps), when measured using a Brookfield digital viscometer, Model DV-II+ Version 3.2 according to the operating instructions set forth in Manual No. M/92-161-H895, such as having a viscosity less than about 5000 cps, such as less than about 1000 cps. Such low viscosity liquid impregnates tend to be more aesthetically pleasing to the user, particularly when the product is a hydrating mask.

The liquid impregnate may include water, isopropyl alcohol, glycols, hydro-alcohols, glycerin, esters, as well as humectants, emollients, penetration enhancers, sensory agents such as menthol and methyl lactate), chelating agents such as EDTA), preservatives such as parabens, and other conventional cosmetic adjuvants, such as dyes, opacifiers (e.g., titanium dioxide and zinc oxide), pigments, and fragrances. Furthermore, the liquid impregnate may include one or more benefits agents as discussed below in the section entitled, "Benefit Agents."

Microcapsules

The product includes a plurality of microcapsules. The microcapsules may be distributed (e.g., uniformly) about the water-insoluble substrate to facilitate contact with a user's skin. The microcapsules have a microcapsule wall surrounding a liquid core. The microcapsule wall is generally configured such that the wall will break, crack, or rupture under an applied stress that is relatively low. For example, the microcapsule wall may be readily fractureable into one or more fragments upon providing a pressure of less than about 1 pound per square inch (psi), such as between about to about 0.5 psi and about 1 psi. Once the microcapsule wall has broken, cracked or ruptured, the liquid core is capable of being released.

The microcapsule wall is generally formed from a material that is substantially insoluble in the liquid core and substantially insoluble in the liquid impregnate (if present). By "substantially insoluble" it is meant that the microcapsule wall is generally resistant to dissolution or salvation from the liquid impregnate or the liquid core during a period of "shelf-storage" time (e.g., from about 6 months or greater). During this period of time, the microcapsule wall generally maintains its ability to contain the liquid core.

For example, for embodiments of the invention in which the liquid impregnate includes a substantial amount of water, the microcapsule wall is substantially insoluble in water.

The microcapsule wall may be formed from or include a water-insoluble polymer, such as an inorganic polymer (e.g. a sol-gel derived silica) or a water-insoluble organic polymer. Exemplary water-insoluble organic polymers include polyamines, polyacrylates, polysaccharides, cyclodextrins, and combinations thereof.

Water-insoluble organic polymers of particular note are thermoset polymers, including polyamines such as those based upon or including monomers such as melamine, urea, and combinations thereof. Suitable polymers include, for example, melamine-formaldehyde resins and urea-formaldehyde resins. Such microcapsules are often referred to as "aminoplast" microcapsules. One such example is polyoxymethyene melamine urea (PMU), commercially available as Pontenza Dimethicone from Reed-Pacific of Dural, Austrialia. Another such example is PMU Microcapsules (32 Micron Encapsulated Mineral Oil and Jojoba Oil), available from 3M Company of St. Paul, Minn. Such polymers may be readily formed into microcapsule walls surrounding a liquid core. The microcapsule walls formed therefrom are highly storage stable, yet sufficiently brittle such that they fracture upon user to relatively low stresses.

The microcapsules may have an average particle size that is in a range from about 1 micron to about 1000 microns, such as between about 100 microns to about 500 microns. By "particle size", it is meant the length of an imaginary line that connects the furthest points on the outer surface of the particle. Furthermore, the microcapsule walls may have a thickness in a range from about 0.01 microns to about 1 micron, such as between about 0.1 microns to about 0.5 microns. The microcapsule walls may be single-layered or multi-layered and may be smooth or irregular in shape.

The microcapsules may be formed from methods such as in-situ polymerization, complex coasservation, or complex precipitation. Examples of forming aminoplast microcapsules surrounding a liquid core and dispersions of such microcapsules are set forth in UK Patent application 2073132A, PCT patent application publication number WO 98/28396, and PCT patent application publication number WO 02/074430. The dyes, perfumes and other "internal phases" (i.e., liquid cores) discussed in these above references may be readily modified by substituting mineral oil and/or other constituents as discussed below in the section entitled "Liquid Core."

Liquid Core

The microcapsules include a microcapsule wall surrounding a liquid core. In one embodiment of the invention, the liquid core is hydrophobic or includes predominantly hydrophobic materials. For example, the liquid core may include a hydrophobic vehicle such as moisturizing oil such as mineral oil or other oil or esters that provide good wetting, spreading, emolliency and/or moisture barrier properties to the skin. Suitable examples of such hydrophobic vehicles include those disclosed in the International Cosmetic Dictionary and Handbook (CTFA, Ninth Edition 2001) under "Skin-Conditioning Agents—Emollient on pages 2930-36. Notable non-limiting examples of hydrophobic vehicles include cetyl alcohol, dimethicone, mineral oil, isohexadecane, isopropyl myristate, lanolin, myristyl myristate, PEG-40 hydrogenated castor oil, phytosterol, shea butter, and combinations thereof. The hydrophobic vehicle may have a specific gravity that is less than 1, for example, in a range from about 0.7 to about 0.95, such as between about 0.80 and about 0.95.

Other suitable ingredients for use in the liquid core include volatile fragrant oils, or various skin benefit agents (see section below entitled, Benefit Agents), particularly those benefit agents that are hydrophobic, compatible with other components of the liquid core, and/or unstable with respect to contact with components that may be present in the liquid impregnate (i.e., outside the microcapsule walls). Benefit agents of particular note that may be included in the liquid core are retinoids such as retinol, Vitamin E, skin-firming agents such as tertiary alkanolamines including dimethyl aminethanol (DMAE), extracts of soy, feverfew, or other plant extracts known for providing benefits to the skin, and peptides such as copper-containing peptides.

Benefit Agents

In one embodiment of the invention, the water-insoluble substrate include one or more benefit agents. What is meant by an "benefit agent" is a compound (e.g., a synthetic compound or a compound isolated from a natural source) that has a cosmetic or therapeutic effect on the skin including, but not limited to, lightening agents, darkening agents such as self-tanning agents, anti-acne agents, shine control agents, anti-microbial agents, anti-inflammatory agents, antifungals, anti-parasite agents, external analgesics, sunscreens, photoprotectors, antioxidants, keratolytic agents, moisturizers, nutrients, vitamins, energy enhancers, anti-perspiration agents, astringents, deodorants, hair growth inhibitors, anti hair-loss agents, hair growth promoters, hair removers, skin-firming agents, anti-callous agents, anti-aging agents such as anti-wrinkle agents, skin conditioning agents, allergy inhibitors, antiseptics, external analgesics, antipruritics, antihistamines, antiinfectives, anticholinergics, vasoconstrictors, vasodilators, wound-healing promoters, peptides, polypeptides, proteins, deodorants, anti-perspirants, film-forming polymers, counterirritants, enzymes, enzyme inhibitors, poison ivy treatment agents, poison oak treatment agent, burn treatment agents; anti-diaper rash treatment agents; prickly heat agents; herbal extracts; flavenoids; sensates; anti-oxidants, keratolytics; sunscreens; and anti-edema agents; and combinations thereof.

In one embodiment of the invention, the agent is selected from, but not limited to, hydroxy acids, benzoyl peroxide, sulfur resorcinol, ascorbic acid and its derivatives, D-panthenol, hydroquinone, octyl methoxycinnimate, titanium dioxide, octyl salicylate, homosalate, avobenzone, polyphenolics, carotenoids, free radical scavengers, spin traps, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper, coenzyme Q10, lipoic acid, amino acids such a proline and tyrosine, lipo amino acids such as caproyloyl glycine and sarcosine, vitamins, lactobionic acid, acetyl-coenzyme A, niacin, riboflavin, thiamin, ribose, electron transporters such as NADH and FADH2, and other botanical extracts, and salt, esters, and derivatives thereof. The benefit agent will typically be present in the composition or product of the invention in an amount of from about 0.001% to about 20% by weight of the liquid impregnate or liquid core, e.g., about 0.01% to about 10% such as about 0.1% to about 5%.

Examples of vitamins include, but are not limited to, vitamin A, a vitamin B such as vitamin B3, vitamin B5, and vitamin B12, vitamin C, vitamin K, and vitamin E, and salts, esters, and derivatives thereof. (e.g., retinyl palmitate, ascorbyl acetate, and tocopherol acetate).

Examples of hydroxy acids include, but are not limited to, glycolic acid, lactic acid, malic acid, salicylic acid, citric acid, and tartaric acid.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbic acid glucoside, magnesium ascorbyl phosphate, and ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isofavonoids and their derivatives (e.g., genistein and diadzein), extracts containing resveratrol and the like. Examples of such natural extracts include grape seed, green tea, pine bark, and propolis.

Examples of botanical extracts include, but are not limited to legumes such as Soy, Aloe Vera, Feverfew, Hedychium, Rhubarb, Portulaca, Cedar Tree, Cinnamon, Witch Hazel, Dandelion, Chinese Angelica, Turmeric, Ginger, Burnet, Houttuynia, Coix Seed, and Thyme. What is meant by a "botanical extract" is a blend of two or more compounds isolated from a plant.

In one embodiment of the invention, the water-insoluble substrate designed for application on the forehead region of the face includes, but is not limited to: oil-control agents such as titanium dioxides, alcohols, botanical extracts, and talc; pore refining agents such as alpha-hydroxy acids, beta-hydroxy acids, and enzymes; anti-acne agents such as benzoyl peroxide, salicylic acid, trichlorcarban, triclosan, azelaic acid, clindamycin, adapalene, erythromycin, sodium sulfacetamide, retinoic acid, and sulfur; oil-absorbing agents such as titanium dioxides and clays; shine control agents such as silicones, alcohols, talc, and clays; dark spot reduction agents such as vitamin C, hydroquinone, botanical extracts, alpha-hydroxy acids, beta-hydroxy acids, and retinoids; and/or wrinkle/fine-line reduction agents such as retinoids, alpha-hydroxy acids, and enzymes.

In another embodiment of the invention, the water-insoluble substrate that is designed for application around the mouth region of the face includes, but is not limited to: hydration/moisturization agents such a glycerin, silicone, glycols, botanical extracts, and esters; pore-refining agents; anti-acne agents; vasodilators such as niacinamide and horsechesnut extract; vasoconstrictors such as caffeine and botanical extracts; skin-lifting agents such as (e.g., copper containing peptides, dimethyaminoethanol, and polymers); skin-firming polymers; wrinkle/fine-line reduction agents; depigmenting/skin lightening agents such as vitamin C, hydroquinone, botanical extracts, alpha-hydroxy acids, beta-hydroxy acids, retinoids, arbutin, and kojic acid; and depilatory/hair reducing agents such as soy extracts, n-acetyl-cysteine, and isoflavones.

The benefit agent(s) may be placed in the liquid core, in the liquid impregnate, or in both. In one embodiment of the invention, one or more benefit agents are segregated according to hydrophilicity/hydrophobicity. For example, hydrophilic benefit agents may be in the liquid impregnate, and hydrophobic benefit agents may be within the liquid core, essentially isolated from the hydrophilic benefit agents until the microcapsules rupture. While various combinations are contemplated, under one non-limiting example, one or more benefit agents are selected from the group consisting of ascorbic acid and its derivatives, alpha-hydroxy-acids, beta-hydroxyacids, alkanolamines, proteins, enzymes, and enzyme activators, and combinations thereof are in the liquid impregnate, and one or more benefit agents are selected from the group consisting of retinoids, tocopherols, enzymes, enzyme activators, and combinations thereof are within the liquid core. In an alternative embodiment of the invention, hydrophobic benefit agents are in the liquid impregnate and hydrophilic benefit agents are within the liquid core.

In one embodiment of the invention, the product comprises an enzyme such as a lignin peroxidase (commercially available from Rakuto Biotechnologies of Yokneam, Israel) and a suitable activator such as a peroxide (e.g., hydrogen peroxide). The enzyme and the activator may be separated by the microcapsule wall. For example, the enzyme may be included in the liquid core and the activator may be included in the liquid impregnate. In another embodiment of the invention, the activator may be included in the liquid core and the enzyme may be include in the liquid impregnate.

Anti-acne Agent

In one embodiment of the invention, one or more of the water-insoluble substrates of the product of the present invention includes an anti-acne agent(s). What is meant by an "anti-acne agent" is a drug product effective in the treatment of acne. Examples of anti-acne agents include, but are not limited to, azelaic acid, clindamycin, adapalene, erythromycin, sodium sulfacetamide, retinoic acid, benzoyl peroxide, sulfur, and salicylic acid.

In one embodiment of the invention, the substrate includes from about 0.01 to about 50 percent, by weight, of the at least one anti-acne agents, e.g., about 0.2 to about 30 percent, by weight, such as about 0.2 to about 15, percent, by weight, of the at least one anti-acne agent.

Other Materials

Various other materials may also be present in the liquid impregnate and/or in the liquid core. These include humectants, emollients, carriers/encapsulation for benefit agents (e.g., liposomes), penetration enhancers, sensory agents (e.g., menthol and methyl lactate), chelating agents (e.g., EDTA), detergents/surfactants/self-foaming agents, and preservatives (e.g., parabens). In addition, the topical compositions useful herein can contain conventional cosmetic adjuvants, such as dyes, opacifiers (e.g., titanium dioxide and zinc oxide), pigments, and fragrances.

Packaging of Product

In one embodiment of the invention, the product is in finished packaged form. In one embodiment, the package is a container such as a plastic, metal or glass tube, tub, pouch or jar containing the water-insoluble substrate. The product may further contain additional packaging such as a plastic or cardboard box for storing one or more of such containers (e.g., a package of two to twenty individual products). Non-limiting examples of material that may be used to manufacture such containers include aluminum, polypropylene, polyethylene, and/or polyesters. In one embodiment of the invention, the package is substantially air-impermeable.

In one embodiment of the invention, the product includes instructions directing the user to apply the water-insoluble substrate to the skin, such as to the face. In one embodiment, where the product contains a liquid impregnate that is present in an amount at least about 5% by weight of the weight of the water-insoluble substrate, the instructions direct the use to apply the product directly to the skin. In another embodiment where the product contains a liquid impregnate that is present in an amount at least about 5% by weight of the weight of the water-insoluble substrate or a product that does not contain any liquid impregnate, the instructions direct the use to apply a liquid to the product prior to application to the skin (e.g. to add water, a toner, or a cleanser to the product).

In one embodiment, the instructions direct the user to apply the product for the benefit of changing the appearance of the tone and/or color of the skin.

Method of Making and Using the Product

The following is a description of a manufacturing procedure for products of the present invention. Other procedures may be used by a person of ordinary skill in the art.

A water-insoluble substrate material, such as a sheet of non-woven optionally perforated or cut to a pre-determined size such a size a shape to fit over a human face, are used. Openings may optionally be cut out of the sheet corresponding to the eyes, nose, and/or mouth. The substrate may then be folded and placed in a plastic pouch housing or other suitable container.

An optional liquid impregnate may be prepared by mixing ingredients such as water and one or more benefit agents together to form a uniform solution. Aminoplast microcapsules may be added to the liquid impregnate and uniformly dispersed within the liquid impregnate. The resulting liquid impregnate having the microcapsules dispersed therein may then be poured into the housing. Alternatively, the impregnate may be sprayed or otherwise distributed about the substrate (e.g., such that the liquid impregnate and microcapsules dispersed therein are absorbed by the substrate). For embodiments of the invention in which there is no liquid impregnate, the capsules may be dusted or dry-sprayed onto the substrate.

The resulting water-insoluble substrate may be individually sealed in the housing or placed along with other water-insoluble substrates together into a single housing. Multiple packaged substrates may be grouped together in an outer container, such as a box.

In one embodiment, the product includes instructions directing the user to, for example, place or position the water-insoluble substrate on the skin and leave it on the skin. For example, the instructions may direct laying the substrate in contact with the skin (e.g., the face) for a period of time, such as from about a ten seconds to about 1 hour (e.g., such as from about 1 minute to about 15 minutes). The user may also be directed to massage any liquid remaining on the skin after removal of the water-insoluble substrate. Such massaging may facilitate imparting improved color/tone uniformity in the skin of the subject.

As an alternative to leaving the product on the skin, the instructions may direct the user to wipe the water-insoluble substrate across the skin to hydrate and/or cleanse the skin.

Through the pressure applied to the water-insoluble substrate by contacting it with the skin, the microcapsules are broken and the contents of the microcapsules are released on the skin. Liquid impregnate may also be expressed from the water-insoluble substrate. The water-insoluble substrate may then be discarded after use.

In one embodiment of the invention, the water-insoluble substrate may be heated, (e.g., to increase the benefit received by the benefit agent and to increase the level of comfort achieved by the user). To that end, in one embodiment of the invention, the product may include instructions directing the user to place the product in warm water or to expose the product to microwaves.

As discussed above, the microcapsules may provide multiple benefits to the user, such as providing improved appearance of tone and texture of the skin (e.g. lightening, redness reduction, sallowness reduction, and enhanced radiance). Hyrdrophobic vehicles such as skin moisturizers as well one or more of a variety of benefit agents may be included in the liquid core of the microcapsules. Such benefit agents may be protected from premature degradation that may otherwise occur from contact with, for example, moisture outside of the microcapsule. Additional benefit agents may be incorporated in the optional liquid impregnate. By separating the additional benefit agents from the liquid core, these additional benefit agents may also have enhanced shelf-stability. Furthermore, the microcapsules may be readily stabilized in a low viscosity impregnate, enhancing consumer appeal.

EXAMPLES

After the invention has been described in general hereinbefore, the following examples are intended to illustrate details of embodiments of the invention, without thereby limiting it in any matter.

Example 1

The following is an example of a hydrating mask that includes a water-insoluble substrate for application to the face. A water-insoluble substrate formed from a sheet of nonwoven fibers, (KP9560, a blend of 55% rayon and 45% pulp, 60 grams per square meter, commercially available from Sansho Shigyo K.K. of Tosa City, Kouchi, Japan) was cut to size a shape to fit a human face. The outer dimensions were about 20.3 cm×23.2 cm. Openings were cut out of the sheet corresponding to the eyes, nose, and mouth. The liquid-insoluble substrate was folded and placed in a plastic pouch housing.

A liquid impregnate was prepared by mixing various ingredients to form a composition that is identical to the composition used as the liquid impregnate for NEUTROGENA Fine Fairness Mask with Vitamin C, commercially available from NEUTROGENA Corporation, Los Angeles, Calif. Aminoplast microcapsules commercially available from Reed Pacific (having a mineral oil liquid core in a weight ratio to the aminoplast resin of about 4:1) were added to the liquid impregnate such that the microcapsules were present in a concentration of 5% by weight. The microcapsules were uniformly dispersed within the impregnate. About 20 grams of the liquid impregnate including the dispersed microcapsules was then poured into the housing such that the water-insoluble substrate absorbed the liquid impregnate and microcapsules. The water-insoluble substrate was removed from the housing and placed upon the face of a user and allowed to remain in contact with the face for a period of time of about 15 minutes. The water-insoluble substrate was then removed and discarded and liquid remaining on the face was allowed to dry.

The hydrating mask was evaluated for its ability to provide immediate increase in whitening, immediate decrease in redness, and immediate decrease in sallowness. Specifically, a CHROMAMETER CR 300 (commercially available from Minolta Co. Ltd., of Osaka, Japan) was used to determine the immediate increase in whitening, immediate decrease in redness, and immediate decrease in sallowness. A test subject's face was cleaned with a facial cleanser and allowed to dry. Baseline CHROMAMETER readings were performed by placing the CHROMAMETER against the cheek of a first test subject, and taking a measurement to obtain a set of L, a, and b (colorimetric) readings. The procedure was repeated such that for each cheek, the three L, three a, and three b readings were obtained and then averaged independently for the subject to obtain an average L value for each cheek, an average a value for each cheek, and an average b value for each cheek. The hydrating mask was then applied to the face of the subject for 15 minutes, after which the mask was removed and the face was allowed to dry completely (in about 10 minutes). Three separate readings were again taken on each cheek, and the three L readings, three a readings, and three b readings were again separately averaged. For each cheek, a difference between the average L value before treatment with the mask and the average "L" value after treatment with the mask was determined. The two differences thus calculated for each cheek were then averaged, and this average was reported as immediate increase in whitening (0=pure black, 100=pure white). Similarly, the difference between the average "a" value before treatment with the mask and the average "a" value after treatment with the mask was determined for each cheek, averaged, and reported as immediate increase in redness (0=pure green, 100=pure red). Similarly, the difference between the average "b" value before treatment with the mask and the average "b" value after treatment with the mask was determined for each cheek, averaged, and reported as immediate increase in sallowness (0=pure blue, 100=pure red).

The immediate increase in whitening, immediate decrease in redness, and immediate decrease in sallowness were respectively determined to be 1.43, 0.58, and −0.34 for the product of Example 1.

Comparative Example 1

A hydrating facial mask was prepared in a similar manner as for Example I, except that no microcapsules were dispersed in the liquid impregnate (Comparative Example I is identical to Neutrogena Fine Fairness Mask with Vitamin C). The immediate increase in whitening, immediate decrease in redness, immediate decrease in sallowness, and immediate increase in radiance were determined to be (respectively) −0.36, 0.19, and −0.12. The whitening and redness results were substantially inferior to Example I, indicating that the microcapsules provided benefits with respect to decrease in whitening and redness.

Examples 2-5

Other examples of suitable liquid impregnates consistent with embodiments of the invention described herein include Examples 2-5 listed below.

| Trade Name | CTFA/INCI Name & Activity | Function | % w/w Ex. 2 | % w/w Ex. 3 | % w/w Ex. 4 | % w/w Ex. 5 |
|---|---|---|---|---|---|---|
| Ascorbyl glucoside | Ascorbyl glucoside | Anti-oxidant; depigmenting agent | 1 | 1 | 1 | 1 |
| Dipotassium glycyrrizate | Dipotassium glycyrrizate | Anti-irritant | 0.05 | 0.05 | 0.05 | 0.05 |
| Glycerin | Glycerin | Moisturizing agent | 10 | 6 | 6 | 6 |
| Disodium EDTA | Disodium EDTA | Chelating agent | 0.2 | 0.2 | 0.2 | 0.2 |
| Sodium PCA | Sodium PCA | Moisturizing agent | 0.1 | 0.1 | 0.1 | 0.1 |
| Allantoin | Allantoin | Anti-irritant | 0.08 | 0.08 | 0.08 | 0.08 |
| Potenza-Diemthicone | Polyoxymethylene Melamine Urea | Skin Conditioner/Opacifier | 2.5 | 5 | 0 | 5 |

-continued

| Trade Name | CTFA/INCI Name & Activity | Function | % w/w Ex. 2 | % w/w Ex. 3 | % w/w Ex. 4 | % w/w Ex. 5 |
|---|---|---|---|---|---|---|
| | Microcapsules with Dimethicone Core | | | | | |
| Niacinamide | Niacinamide | Depigmentation agent | 0.00 | 2.5 | 2.5 | 2.5 |
| Firmenich Fragrance Fair Beauty | Fragrance | Fragrance | 0.04 | 0.04 | 0.04 | 0.04 |
| Hexylene glycol | Hexylene glycol | Skin conditioning agent | 1 | 1 | 1 | 1 |
| Keltrol | Xanthan Gum | Viscosity modifier | 0.2 | 0.2 | 0.2 | 0.2 |
| Mekkins M | Methylparaben | Preservative | 0.2 | 0.2 | 0.2 | 0.2 |
| Mekkins E | Ethylparaben | Preservative | 0.1 | 0.1 | 0.1 | 0.1 |
| Sodium hydroxide | Sodium hydroxide | PH adjuster | 0.27 | 0.27 | 0.27 | 0.27 |
| Dermacryl AQF | Acrylates copolymer | Opacifying agent | 0 | 0 | 0 | 3 |
| Deionized Water | Water | Vehicle | 84.26 | 83.2 | 88.26 | 80.26 |

The liquid impregnates are made by adding the water to a suitable mixing vessel (the main vessel) and sequentially adding ascorbyl glucoside, dipotassium glycyrrizate, disodium EDTA, sodium PCA, allantoin, and niacinamide. In a separate vessel glycerin, methylparaben, and ethyl paraben are sequentially added to the separate vessel and are heated to 80 degrees Celsius until fully dissolved. This second mixture is added to the main vessel. Xanthan gum and hexylene glycol is separately mixed until homogeneous to form a third mixture, after which this third mixture is added to the main vessel. Sodium hydroxide is added to the main vessel, followed by acrylates polymer, polyoxymethylene Melamine Urea Microcapsules (Examples 2, 3 and 5 only), and the fragrance. For examples 2, 3 and 5, about 24 grams of the impregnate having the microcapsules suspended therein is added to a 203 mm×232 mm piece of 60 gsm, KP9560 (Sansho Shigyo K.K.) rayon/pulp non-woven fabric.

For Example 4, 1.2 grams of Polyoxymethylene Melamine Urea Microcapsules is added to the fabric, followed by 22.8 grams of the liquid impregnate.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

We claim:

1. A product for application to the skin comprising: (i) a water-insoluble substrate; (i) a liquid impregnate having a viscosity of less than about 10,000 cps, wherein said liquid impregnate is present in a weight ratio to the water-insoluble substrate that is greater than about 5%; (iii) a plurality of microcapsules comprising a microcapsule wall surrounding a liquid core, wherein the microcapsule wall comprises a polyamine; and a skin lightening agent.

2. The product of claim 1, wherein the microcapsule wall is readily fractureable into one or more fragments upon pressure of less than about 1 psi.

3. The product of claim 1, wherein said liquid impregnate is present in a weight ratio to the water-insoluble substrate that is greater than about 50%.

4. The product of claim 1 wherein the polyamine comprises monomers of melamine, urea, and combinations thereof.

5. The product of claim 1 wherein the microcapsules have an average particle size that is in a range from about 100 micron to about 500 microns.

6. The product of claim 1 wherein the liquid core comprises a benefit agent selected from a group consisting of a retinoid, a tocopherol, an alkanolamine, an enzyme, and salts and esters thereof.

7. The product of claim 1 wherein the water-insoluble substrate comprises a non-woven, fibrous material.

8. A method of delivering a benefit agent to an expanse of skin, comprising: (a) contacting the skin with a product comprising a water-insoluble substrate, a liquid impregnate, a plurality of microcapsules comprising a microcapsule wall, the microcapsule wall comprising a polyamine, wherein the microcapsule wall surrounds a liquid core, and wherein the product further comprises a skin lightetning agent, wherein said contacting comprises laying said substrate in contact with said expanse of skin for a period of time, and wherein said contact ruptures the microcapsule wall of said microcapsules; and (b) transferring an amount of said benefit agent from the product to the skin.

9. The method of claim 8, wherein said liquid impregnate is present in a weight ratio to the water-insoluble substrate that is greater than about 50%.

10. A method of claim 8, wherein said benefit agent is comprised within said microcapsule.

11. A method of claim 8, wherein the microcapsule wall is readily fractureable into one or more fragments upon pressure of less than about 1 psi.

12. A method of treating an expanse of skin, comprising:
    (a) contacting the skin with a product according to claim 1, wherein said contacting comprises laying said substrate in contact with said expanse of skin for a period of time, and wherein said contact ruptures the microcapsule wall of said microcapsules; and
    (b) removing said product from said expanse of skin, thereby providing an increase in skin whitening.

13. A method of claim 12, wherein said liquid impregnate has a viscosity less than about 10000 cps.

14. A method of claim 12, wherein said liquid impregnate has a viscosity less than about 1000 cps.

15. A method of claim 12, wherein said expanse of skin includes the face.

16. A method of claim 12, wherein said period of time is from about ten seconds to about one hour.

* * * * *